United States Patent
Kühn et al.

(10) Patent No.: US 6,916,484 B1
(45) Date of Patent: Jul. 12, 2005

(54) AQUEOUS PHARMACEUTICAL COMPOSITION CONTAINING MOXIFLOXACIN OR SALTS THEREOF

(75) Inventors: Bernd Kühn, Köln (DE); Hans-Friedrich Mahler, Köln (DE); Michael Eisele, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/049,094

(22) PCT Filed: Jul. 25, 2000

(86) PCT No.: PCT/EP00/07099

§ 371 (c)(1),
(2), (4) Date: Feb. 5, 2002

(87) PCT Pub. No.: WO01/10408

PCT Pub. Date: Feb. 15, 2001

(30) Foreign Application Priority Data

Aug. 6, 1999 (DE) .......................... 199 37 115

(51) Int. Cl.$^7$ ................................. A61F 2/02
(52) U.S. Cl. ...................................... 424/423
(58) Field of Search ......................... 424/423

(56) References Cited

U.S. PATENT DOCUMENTS

| | | | |
|---|---|---|---|
| 4,990,517 A | 2/1991 | Petersen et al. | 514/300 |
| 5,059,597 A | 10/1991 | Petersen et al. | 514/224.5 |
| 5,084,276 A | 1/1992 | Yunker et al. | 424/422 |
| 5,416,096 A | 5/1995 | Petersen et al. | 514/312 |
| 5,563,149 A | 10/1996 | Jung et al. | 514/300 |
| 5,607,942 A | 3/1997 | Petersen et al. | 546/200 |
| 5,811,130 A | 9/1998 | Boettner et al. | 424/643 |
| 6,103,925 A | 8/2000 | Urbahns et al. | 560/83 |

FOREIGN PATENT DOCUMENTS

| | | |
|---|---|---|
| EP | 0534860 A1 * | 3/1993 |
| EP | 0507851 | 2/1997 |
| WO | 0018386 | 6/2000 |
| WO | 0025765 | 11/2000 |

OTHER PUBLICATIONS

Nagy, L., Gajda, J., Schrantz, K., Burger, K., "Spectroscopic Studies of Iron(III) Complexes of D–Saccharose and D–Glucose in the Solid State and in Solution", J. Radioanal. Nucl. Chem., 209: 225–234 (1996).

Weber, G., "Investigation of the Stability of Metal Species With Respect to Liquid Chromatographic Separations", Fresenius J. Anal. Chem., 346: 639–642 (1993).

Veres, S., Strurcz, E., "A Matrixhatas Vizsgalata Cukortipusu Hemiontartalmanak Atomabszorpcios Meghatarozasanal", Magy. Kem. Foly., 93: 199–204 (1987).

Rao, C., Geetha, K., Raghavan, S., "Fe(III) Complexes of D–Glucose and D–Fructose", BioMetals, 7: 25–29 (1994).

Ballow, C., Lettieri, J., Agarwal, V., Liu, P., Stass, H., and Sullivan J., "Absolute Bioavailability of Moxifloxacin", Clin. Ther., 21(3): 513–522 (1999).

Siefert, H. M., Domdey–Bette, A., Henninger, K., Hucke, F., Kohlsdorfer, C., and Stass, H. H., "Pharmacokinetics of the 8–Methoxyquinolone, Moxifloxacin: A Comparison in Humans and Other Mammalian Species", J. Antimicrobial Chemotherapy, 43(B): 69–76 (1999).

Wise, R., Andrews, J. M., Marshall, G., and Hartman, G., "Pharmacokinetics and Inflammatory–Fluid Penetration of Moxifloxacin Following Oral or Intravenous Administration", Antimicrobial Agents and Chemotherapy, 43(6): 1508–1510 (Jun. 1999).

* cited by examiner

Primary Examiner—Carlos A. Azpuru

(57) ABSTRACT

The invention relates to an aqueous pharmaceutical composition containing moxifloxacin and less than 10 ppb iron.

35 Claims, No Drawings

AQUEOUS PHARMACEUTICAL COMPOSITION CONTAINING MOXIFLOXACIN OR SALTS THEREOF

The present invention relates to an aqueous pharmaceutical formulation which comprises moxifloxacin or a salt thereof and isotonizing agents and whose iron content is less than 20 ppb. Furthermore, the present invention relates to the use of mono- and disaccharides and/or glycerol, the iron contents of which are below certain limits, for preparing an aqueous pharmaceutical formulation of moxifloxacin or a salt thereof and to processes for preparing aqueous pharmaceutical formulations of moxifloxacin or a salt thereof in which isotonizing agents having iron contents below certain limits are used.

Moxifloxacin (INN—International Nonproprietary Name) is an antibiotic from the class of the quinolonecarboxylic acids of the following formula:

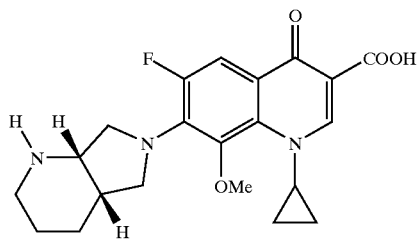

1-cyclopropyl-7-([S,S]-2,8-diazabicyclo[4.3.0]non-8-yl)-6-fluoro-1,4-dihydro-8-methoxy-4-oxo-3-quinolonecarboxylic acid It is a highly effective anti-infective agent and was described for the first time in EP-A-0 350 733. However, EP-A-0 350 733 does not describe any pharmaceutical preparations which are suitable for parenteral administration. Such a solution for infusion, which can be administered parenterally, is needed, in particular for treating patients in intensive care units who cannot be treated orally.

For formulating solutions for infusion which are acceptable, it is necessary to adjust the osmolality to the physiological conditions of the organism (Sucker/Fuchs/Speiser; Pharmazeutische Technologie). Relatively pronounced hypo- or hyperosmotic variations can result in erythrocyte damage and/or tissue irritation. The i.v. administration of relatively strong hypoosmotic solutions leads to haemolysis, and administration of relatively large amounts of hyperosmotic solutions leads to plasmolysis. Hypoosmotic solutions contain fewer dissolved molecules or ions than are present in the blood or the tissue fluid. In this case, isotonization has to be carried out by addition of sodium chloride, glucose or mannitol, etc. (Bauer/Frömming/Führer, Pharmazeutische Technologie). A range from 270 to 350 mOsmol/kg is considered to be isotonically suitable.

Commercial isotonic solutions are, for example, a 5% strength glucose solution or a 0.9% strength sodium chloride solution.

EP-A-534 860 describes formulations of the quinolonecarboxylic acid antibiotic sparfloxacin with monocarboxyl-polyhydroxy acids or lactones thereof, such as, for example, ascorbic acid, and with glucose or glycerol as isotonizing additive. The invention is based on improving the solubility of sparfloxacin by means of monocarboxyl-polyhydroxy acids to obtain acceptable, isotonic or hypertonic formulations of suitable concentration.

U.S. Pat. No. 5,563,149 describes the formulation of aqueous solutions of pyridonecarboxylic acids and esters and salts thereof as antibiotics as ready-to-use solutions for injection or infusion or concentrates for injection or infusion. Details about isotonization additives or about the tonicity of the formulations are not given. The object of said invention is to improve the solubility of the pyridonecarboxylic acids described.

EP-A0 507 851 B1 describes formulations comprising quinolonecarboxylic acid/metal ion acid complexes. It has been found that the solubility of the active compound is increased when polyvalent metal ions in the form of magnesium, calcium, manganese, zinc, cadmium, aluminum, cerium or iron ions are added, as a consequence of complex formation at neutral pH. Such formulations are described as being chemically and physically stable, even in the presence of glucose for isotonization, and are better tolerated, owing to a neutral pH.

U.S. Pat. No. 5,811,130 describes metal ion complexes with danofloxacin where in particular magnesium and zinc ions are used for complex formation and with which the solubility of danofloxacin is increased considerably. Formulations with high active compound concentration for subcutaneous injection are described which can only be achieved by the improved solubility of the metal ion/active compound complexes in water.

Furthermore, U.S. Pat. No. 5,084,276 teaches the use of quinolonecarhoxylic acid/metal ion complexes, for example with magnesium, calcium, manganese, zinc, cadmium, iron-(II) and iron-(III) or cerium-(IV) ions for complexing the active compounds temafloxacin, toxyfloxacin or pefloxacin, where the active compound complexes are used together with auxiliaries for reducing irritation of the veins. The formulations for parenteral infusion described are isotonized with glucose.

During the development work on moxifloxacin, it was surprisingly found that conventional isotonization by addition of 5% glucose or other sugars or sugar alcohols, such as 2.5% glycerol; is not possible in the case of moxifloxacin, as it always gives unstable solutions. This instability manifests itself by the occurrence of subvisual particles in the solution, the number of which exceeds the range permissible by the pharmacopoeias (USP XXIII, BP93). During storage, brown amorphous particles are formed, which frequently only occur after 4–8 weeks of storage at 40° C., and the number of which increases further during storage. At room temperature or on storage in the refrigerator, the formation of these particles is slower.

It is an object of the present invention to provide, despite these formulation problems, isotonized and thus acceptable and at the same time storage-stable pharmaceutical formulations suitable for use as solutions for infusion.

The inventors found that the particle formation is caused by a three-fold interaction between moxifloxacin and/or its salts, iron and sugar or sugar alcohols, such as glycerol. This was surprising, since similar phenomena in the formulation of parenteral formulations of quinolonecarboxylic acid have hitherto not been known, and in particular EP 0 507 851, U.S. Pat. Nos. 5,811,130 and 5,084,276 utilize the interaction of polyvalent metal ions with quinolonecarboxylic acids for stabilization and increasing solubility.

Surprisingly, it has furthermore been found that even traces of iron in the formulation which are within the detection limit in the lower ppb range have destabilizing action. It has been found that, in addition to the active compound itself, the isotonization auxiliaries sugar and/or sugar alcohols, such as glycerol, which, besides water, form the highest proportion by weight in the formulation, are a substantial source of trace iron contamination. Complex formation of iron with sugars has been described in various references (Nagy et al., 1996; Weber, 1993; Veres et al., 1987; Ladesic et al., 1992; Rao et al., 1993).

Accordingly, the invention provides aqueous pharmaceutical formulations comprising moxifloxacin or a salt thereof and at least one isotonizing agent selected from the group consisting of sugars and sugar alcohols and which are characterized by an iron content of less than 20 ppb, preferably less than 10 ppb. In particular in cases where glycerol is used, the upper limit for the iron content is preferably 10 ppb.

For the purpose of the present invention, an aqueous pharmaceutical formulation is a formulation which, as solvent, comprises substantially water. However, depending on the infusion volume to be administered, it may optionally comprise water-miscible organic solvents in a proportion of up to 50% (w/v), preferably less than 30% (w/v), as long as this does not impair the physiological acceptability of the formulation. Particularly preferably, the aqueous pharmaceutical formulation of the invention comprises substantially no organic solvents, except for the isotonizing agent glycerol used according to the invention.

Moxifloxacin and salts thereof include moxifloxacin in its betaine form and salts thereof. Salts of moxifloxacin are, for example, acid addition salts, such as salts of hydrochloric acid, sulfuric acid, acetic acid, lactic acid, etc., and salts with bases, such as sodium hydroxide, potassium hydroxide, etc. According to the invention, particular preference is given to moxifloxacin hydrochloride.

Sugars which can be used according to the invention include monosaccharides such as glucose, fructose, mannose, galactose, arabinose, xylose and ribose, etc., and also oligosaccharides such as disaccharides (maltose, lactose, sucrose, trehalose, etc.) and trisaccharides (e.g. raffinose, maltotriose, etc.). Particular preference is given to glucose, maltose and sucrose. Very particular preference is given to glucose.

Sugar alcohols which can be used according to the invention include, for example: glycerol, mannitol, xylitol, dulcitol, arabitol, etc. Particular preference is given to glycerol and mannitol. Very particular preference is given to glycerol.

Expediently, the aqueous pharmaceutical formulation of the invention comprises less than 20 ppb of iron (ppb means "parts per billion", corresponding to 1 part by weight of iron per 1 billion parts by volume, i.e., for example, of the pharmaceutical formulation) or less than 20 µg/l (20 g/l 000 000 000 ml), based on the determination in liquids, or less than 20 µg/kg, based on the determination in solids. At these orders of magnitude, an iron content can be determined by atomic absorption spectroscopy (AAS). Since, at such low iron contents of 20 ppb (or, preferably, 10 ppb), the measurements by AAS can be accompanied by variations of the measured values, the iron content of the pharmaceutical formulation of the invention is less than 20 ppb (10 ppb) if the arithmetic mean of at least 6 independent individual determinations by AAS is below 20 ppb (or 10 ppb), respectively.

Expediently, the aqueous pharmaceutical formulation of the invention comprises 0.02% (w/v) (0.02% w/v means 0.02 g/100 ml) to 2.4% (w/v), preferably from 0.1 to 0.5% (w/v), particularly preferably from 0.16 to 0.2% (w/v) of moxifloxacin or their salts, preferably moxifloxacin hydrochloride. These amounts by weight are based on the total volume of the formulation.

The amount of the isotonizing agent used according to the invention is expediently chosen such that preparations having a tonicity of up to 350 mOsmol/kg, preferably from 270 to 330 mOsmol/kg, are obtained.

The aqueous pharmaceutical formulation of the invention expediently comprises from 150 mmol/l to 350 mmol/l, preferably from 250 mmol/l to 350 mmol/l particularly preferably from 270 mmol/l to 330 mmol/l of at least one sugar as, for example, mentioned above. Very particularly preferably, the pharmaceutical formulation comprises from 275 mmol/l to 305 mmol/l of glucose.

The aqueous pharmaceutical formulation of the invention expediently comprises from 150 mmol/l to 350 mmol/l, preferably from 250 mmol/l to 350 mol/l particularly preferably from 270 mmol/l to 330 mmol/l of at least one sugar alcohol. Very particularly preferably, the pharmaceutical formulation comprises from 270 mmol/l to 305 mmol/l of sugar alcohol, such as, for example, glycerol.

The aqueous pharmaceutical formulation of the invention may also comprise a combination of sugars and sugar alcohols. By way of example, a formulation may be mentioned which comprises from 0 to 350 mmol/l of sugar alcohol, such as glycerol, and from 350 mmol/l to 0 mmol/l of at least one monosaccharide and/or oligosaccharide.

Since, as mentioned above, the main contamination with iron usually occurs through the isotonizing agent used according to the invention, the aqueous pharmaceutical formulation of the invention is generally prepared using monosaccharides, oligosaccharides and/or sugar alcohols having iron contents of less than $6.5 \times 10^{-4}$ mmol of Fe per mole of sugar or sugar alcohol, such as glycerol. An iron content of $6.5 \times 10^{-4}$ mmol of Fe per mole of glucose corresponds to about 200 ppb. An iron content of $6.5 \times 10^{-4}$ mmol of Fe per mole of glycerol corresponds to about 400 ppb. Commercial glucose grades generally have iron contents of from 300 to 600 ppb of Fe, since glucose forms complexes with iron which lead to an enrichment of Fe in the glucose (see, for example, Nagy L. et al., J. Radioanal-Nucl-Chem., September 1996, 209 (1), 225–234; Weber G., Fresenius-J-Anal-Chem., June–July 1993; 346 (6–9): 639–642; Veres S., Magy-Kem-Foly., May 1987; 93 (5): 199–204; Ladesic B. et al.: J. Inorg. Biochem.; 48, 55–62 (1992) and Rao C. P. et al., BioMetals Vol 7, 1994; 25–29).

Owing to the upper limit of the iron content of the formulation, the following equation has to apply to the sum of the iron contaminants of the various starting materials:

$$\sum_{i=1}^{n}(x_i \ast y_i/100) \leq 20 \text{ ppb}$$

where x correspond to the numeric values of the components i in the composition in % (w/v), y is the amount of iron in component i in ppb and $$\sum_{i=1}^{n} x_i = 100$$

For a 0.2% strength (w/v) moxifloxacin formulation with 2.5% (w/v) of glucose and 2.5% (w/v) of mannitol, for example, the following results for the isotonization:

| No. | Feedstock | Quantity $x_i$ [% w/v] | Iron content $y_i$ [ppb] |
|---|---|---|---|
| 1 | Moxifloxacin HCl | 0.2 | 1000 |
| 2 | Glucose | 2.5 | 50 |
| 3 | Mannitol | 2.5 | 50 |
| 4 | Water for injection | 94.8 | 5 |

Calculation: $(x_1*y_1/100)+(x_2*y_2/100)+(x_3*y_3/100)+(x_4*y_4/100) \leq 20$ ppb $(0.2*1000/100)+(2.5*50/100)+(2.5*50/100)+(94.8*5/100) \leq 20$ ppb $2+1.25+1.25+4.74=9.24$ ppb The iron content of the water for injection is below the detection limit of 10 ppb. The estimated value for the calculation is an iron concentration of 5 ppb.

The aqueous pharmaceutical formulation of the invention serves expediently for parenteral administration. Parenteral administration includes, for example, intravenous, intra-arterial, subcutaneous, intramuscular and intraperitoneal administration, intravenous administration being the most important. A dose which is considered to be suitable is 400 mg of active compound, based on the betaine form, for intravenous infusion once per day. The daily infusion volume administered should not exceed 200 to 250 ml. At an amount of active compound of 400 mg, this results in an active compound concentration of about 0.2% (w/v) corresponding to 400 mg/200 ml.

The aqueous pharmaceutical formulation of the invention may, in addition to the ingredients used according to the invention, comprise further auxiliaries which are customary in the field of parenteral administration forms, such as, for example, acids and bases for adjusting the pH, and customary preservatives and antioxidants.

The present invention furthermore relates to the use of at least one sugar, the iron content of which is less than $6.5 \times 10^{-4}$ mmol of Fe per mole of sugar, and to the use of sugar alcohols, such as, for example, glycerol, the iron content of which is less than $6.5 \times 10^{-4}$ mol of Fe per mol of glycerol, for preparing an aqueous pharmaceutical formulation of moxifloxacin or a salt thereof.

Corresponding feedstock grades are commercially available from a few manufacturers. By way of example, glucose type C*2010 (Cerestar) may be mentioned.

To keep the iron that is introduced into the pharmaceutical formulation of the invention below the limit for the finished solution of 20 ppb, the apparatus used for the manufacture should furthermore be selected with a view to non-corrodability and corrosion resistance. Since any possibility of introducing traces of iron into the product has to be avoided, use is to be made, in particular, of apparatus made of glass or enamel-coated steel containers or, if appropriate, plastic or plastic-coated material (for example Teflon, PE, PP, etc.). Plants made of pharmaceutical-grade steel (1.4404, 1.4435, 1.4571, 316-grade steel, etc.) are also suitable; however, care is to be taken to minimize contact times, and it has to be made sure that al parts which are in contact with the product are corrosion-free. Relatively long residence times of more than 12 hours have to be avoided, if possible.

If new steel apparatus is used, the surfaces have to be passivated or subjected to artificial ageing and, if appropriate, repeated pre-treatment with the product has to be carried out for "rinsing", in order to remove free iron from the surfaces and to prevent contamination of the product during further preparation.

Using the invention, it is possible to prepare stable and acceptable solutions for infusion comprising the active compound moxifloxacin. It is possible to formulate finished solutions for infusion which are easy to handle. The solutions can be provided both in the form of ampoules or infusion bottles made of glass and in the form of flexible infusion bags or bottle packs, etc.

The inventors also discovered that the above-described interaction of sugar- or sugar-alcohol-containing solutions of moxifloxacin with iron ions does not immediately, but only after a certain time, during storage, lead to the undesirable particle formation. Accordingly, freshly prepared solutions of moxifloxacin with sugars and/or sugar alcohols have, even if they have relatively high iron contents, a sufficient stability against the formation of particles for the period of use of, preferably, up to 12 hours after preparation. Thus, the problem to be solved by the invention can also be overcome by iron-containing solutions for infusion which are used immediately after preparation. Here, it is expedient to use a process in which a pre-formed concentrated aqueous solution of moxifloxacin or a salt thereof and a pre-formed solution of the sugar and/or the sugar alcohols are mixed with one another. Accordingly, the invention also provides a process for preparing an aqueous formulation of moxifloxacin or a salt thereof, wherein a solution of moxifloxacin or a salt thereof having a moxifloxacin concentration or moxifloxacin salt concentration of from more than 0.2% (w/v) to the saturation concentration at room temperature of moxifloxacin or the salt thereof is, using a sugar- and/or sugar-alcohol-containing infusion carrier solution, adjusted to a use concentration suitable for parenteral administration. A use concentration suitable for parenteral administration has the osmolalities or concentrations mentioned for the formulations according to the invention. If such a process is used, it is also possible to use an aqueous solution for infusion, the iron content of which considerably exceeds 20 ppb. However, the solutions for infusion prepared from solution for infusion concentrate and infusion carrier solution have to be infused immediately after preparation to ensure satisfactory pharmaceutical quality. The formulation from an infusion concentrate immediately before use has the advantage that, in clinical application, a large number of available infusion carrier solutions can be used for diluting the moxifloxacin to use concentrations, it being possible to carry out an individual therapy. The infusion concentrate can be prepared in a simple manner by dissolving the active compound in water. A particularly suitable infusion concentrate is a solution of moxifloxacin hydrochloride having a concentration of from more than 0.2% (w/v) to 2.4% (w/v) (based on the amount of moxifloxacin), which is particularly suitable for preparing a pharmaceutical for parenteral administration. Particularly advantageous for practical use by physicians or care personnel is a combination preparation, comprising, separated from one another, an aqueous solution of moxifloxacin hydrochloride in water having a moxifloxacin hydrochloride concentration (based on the amount of moxifloxacin) of from more than 0.2% (w/v) to 2.4% (w/v) and an aqueous solution comprising sugar and/or sugar alcohols. The finished aqueous solution for infusion can then be prepared immediately before infusion by simple mixing of the two solutions. The concentrated aqueous solution of moxifloxacin id hydrochloride preferably contains from 0.4% (w/v) to 2.4% (w/v) of moxifloxacin (calculated as betaine). The maximum concentration of the aqueous solution is limited by the saturation solubility of moxifloxacin hydrochloride of about 2.4% (w/v). The active compound concentrate preferably comprises from 1.0 to 2.0% (w/v) of moxifloxacin (calculated as betaine), particularly preferably 2.0% (w/v) of moxifloxacin (calculated as betaine). The active compound concentrate is filled into suitable containers and sterilized in a suitable manner. The containers can be made of glass or plastic. The container materials may comprise substances which impart special protection to the contents, such as, for example, protection against light or protection against oxygen. The active compound concentrate is diluted to the use concentrations of the moxifloxacin formulations according to the invention by mixing with sugar- and/or sugar-alcohol-containing solutions. If appropriate, the solutions used for diluting the active compound concentrate may, in addition to sugars and/or sugar alcohols, also comprise salts with sodium, potassium, calcium, magnesium, etc., such as chlorides, carbonates, sulfates, acetates, gluconates, lactates, malates, etc. It is also possible to use customary, commercially available infusion carrier solutions for diluting the active compound concentrate.

EXAMPLES

Example 1

Isotonic Solution for Infusion 0.2% (400 mg/200 ml) Glucose

| | | |
|---|---|---|
| Moxifloxacin-HCl, 1000 ppb | Fe | 0.2%* |
| Glucose, 35 ppb | Fe | 5.0% |
| Water for injection, 5 ppb | Fe | 94.8% |

*Active compound content based on the betaine

The iron content of the solution for infusion is 8.5 ppb.

Calculation: $(x_1*y_1/100)+(x_2*y_2/100)+(x_3*y_3/100) \leq 20$ ppb $(0.2*1000/100)+(5*35/100)+(94.8*5/100) \leq 20$ ppb $2+1.75+4.74 = 8.5$ ppb In a parallel experiment, iron in the form of an iron-III chloride solution is added to the formulation during preparation. The iron content of the finished solution is, according to AAS determination, about 76 ppb.

For preparation, water for injection is initially charged in an enamel-coated steel container, and moxifloxacin and glucose are dissolved therein with stirring at RT. The solution has a pH of about 4.4. The solution is then filtered through a filter having a pore size of 0.45 μm into an enamel-coated intermediate container, and in each case 200 ml are filled into infusion bottles. The filled bottles are sterilized in an autoclave at 121° C. for 20 min.

Examination of the particles after storage shows the following results:

| | | Number of brown particles ≥ 25 μm/ml | |
|---|---|---|---|
| Storage time | Temperature | Without addition of Fe 8.5 ppb of Fe | With addition of Fe about 76 ppb of Fe |
| Start | — | 0.00 | 0.04 |
| 6 weeks | 6° C. | 0.02 | 0.04 |
| | 25° C. | 0.01 | 0.19 |
| | 40° C. | 0.08 | 1.20 |
| 22 weeks | 25° C. | 0.07 | 0.48 |

The low-iron formulation is stable, whereas the relatively iron-rich formulation shows a considerable increase of the particle values during storage.

Example 2

Isotonic Solution for Infusion 0.2% (200 mg/100 ml), Glycerol

| | | |
|---|---|---|
| Moxifloxacin-HCl, 1000 ppb | Fe | 0.2%* |
| Glycerol, 70 ppb | Fe | 2.5% |
| Water for injection, 5 ppb | Fe | 97.3% |

*Active compound content based on the betaine

The iron content of the solution for infusion is 8.6 ppb.

Calculation: $(x_1*y_1/100)+(x_2*y_2/100)+(x_3*y_3/100) \leq 10$ ppb $(0.2*1000/100)+(2.5*70/100)+(97.3*5/100) \leq 10$ ppb $2+1.75+4.87 = 8.6$ ppb For preparation, water for injection is initially charged in a 20l glass bottle, and moxifloxacin and glycerol are dissolved therein with stirring at RT. The solution has a pH of about 4.4. The solution is then filtered through a filter having a pore size of 0.22 μm into an enamel-coated intermediate container, and in each case 100 ml are filled into infusion bottles. The filled bottles are sterilized in an autoclave at 121° C. for 20 min.

Examination of the particles after storage shows the following results:

| | | Number of brown particles ≥ 25 μm/ml |
|---|---|---|
| Storage time | Temperature | (Limit value 2/ml) |
| Start | — | 0.00 |
| 6 weeks | 6° C. | 0.02 |
| | 25° C. | 0.04 |
| | 40° C. | 0.01 |
| 13 weeks | 40° C. | 0.33 |
| 22 weeks | 25° C. | 0.01 |

The formulation is stable with respect to particle formation.

Example 3

Isotonic Solution for Infusion 0.2% (200 mg100 ml), Mannitol

| | | |
|---|---|---|
| Moxifloxacin-HCl, 1000 ppb | Fe | 0.2%* |
| Mannitol, 150 ppb | Fe | 5% |
| Water for injection, 5 ppb | Fe | 94.8% |

*Active compound content based on the betaine

The iron content of the solution for infusion is 14.2 ppb.

Calculation: $(x_1*y_1/100)+(x_2*y_2/100)+(x_3*y_3/100) \leq 20$ ppb $(0.2*1000/100)+(5*150/100)+(94.8*5/100) \leq 20$ ppb $2+7.5+4.74 = 14.2$ ppb For preparation, water for injection is initially charged in a 20l glass bottle, and moxifloxacin and glycerol are dissolved therein with stirring at RT. The solution has a pH of about 4.4. The solution is then filtered through a filter having a pore size of 0.22 μm into an enamel-coated intermediate container, and in each case 100 ml are filled into infusion bottles. The filled bottles are sterilized in an autoclave at 121° C. for 20 min.

Examination of the particles after storage shows the following results:

| Storage time | Temperature | Number of brown particles ≥ 25 μm/ml (Limit value 2/ml) |
|---|---|---|
| Start | — | 0.01 |
| 6 weeks | 6° C. | 0.02 |
| | 25° C. | 0.06 |
| | 40° C. | 0.03 |
| 13 weeks | 40° C. | 0.99 |
| 22 weeks | 25° C. | 0.02 |

The formulation is stable with respect to particle formation.

Example 4
Infusion Concentrate 2% (w/v) (400 mg/20 ml)
Moxifloxacin hydrochloride 400 mg (calculated as betaine)
Water for injection ad 20 ml The water is initially charged in a mixing tank made of stainless steel of pharmaceutical quality, and the moxifloxacin hydrochloride is dissolved therein with stirring. The solution is filtered through a 0.2 μm filter and in each case 20 ml are filled into injection bottles made of glass, which are sealed and sterilized.

For use, the content of the injection bottle (400 mg of moxifloxacin in 20 ml) is removed using a syringe and, under aseptic conditions, added to 180 ml of a commercial 5% glucose solution and mixed. An isotonic solution for infusion having a concentration of 400 mg/200 ml, which corresponds to 0.2% (w/v), is obtained.

What is claimed is:

1. An aqueous pharmaceutical formulation comprising moxifloxacin or a salt thereof and at least one isotonizing agent selected from the group consisting of sugars and sugar alcohols, characterized in that it comprises less than 10 ppb of iron.

2. An aqueous pharmaceutical formulation as claimed in claim 1, characterized in that it comprises moxifloxacin or a salt thereof in an amount of from 0.02 to 2.4% (w/v) (based on the amount of moxifloxacin) and at least one of the isotonizing agents in such an amount that preparations having a tonicity of up to 350 mOsmol/kg are obtained.

3. The aqueous pharmaceutical formulation as claimed in claim 1, characterized in that it comprises isotonizing agents in such an amount that solutions having a tonicity of from 270 to 330 mOsmol/kg are obtained.

4. The aqueous pharmaceutical formulation as claimed in any of claims 1 to 3, characterized in that it comprises from 250 to 350 mmol/l of sugar.

5. The aqueous pharmaceutical formulation as claimed in any of claims 1 to 3, characterized in that it comprises from 250 to 350 mmol/l of sugar alcohol.

6. The aqueous pharmaceutical formulation as claimed in any of claims 1 to 3, characterized in that it comprises from 0 to 350 mmol/l of sugar alcohol and from 350 to 0 mmol/l of at least one monosaccharide or oligosaccharide.

7. The aqueous pharmaceutical formulation as claimed in any of claims 1 to 3, characterized in that it comprises glucose as isotonizing agent.

8. The aqueous pharmaceutical formulation as claimed in any of claims 1 to 3, characterized in that it is prepared using at least one monosaccharide or oligosaccharide, the iron contents of which are less than $6.5 \times 10^{-4}$ mmol/mol of monosaccharide or oligosaccharide.

9. The aqueous pharmaceutical formulation as claimed in any of claims 1 to 3, characterized in that it is prepared using sugar alcohol, the iron content of which is less than $6.5 \times 10^{-4}$ mmol/mol of sugar alcohol.

10. An aqueous pharmaceutical formulation as claimed in any of claims 1 to 3, characterized in that it comprises moxifloxacin hydrochloride.

11. An aqueous pharmaceutical formulation as claimed in any of claims 1 to 3 for parenteral administration to humans and animals.

12. An aqueous pharmaceutical formulation of moxifloxacin or a salt thereof comprising a monosaccharide, the iron content of which is less than $6.5 \times 10^{-4}$ mmol/mol of monosaccharide.

13. An aqueous pharmaceutical formulation of moxifloxacin or a salt thereof comprising a disaccharide, the iron content of which is less than $6.5 \times 10^{-4}$ mmol/mol of disaccharide.

14. A process for preparing an aqueous pharmaceutical formulation of moxifloxacin or a salt thereof, characterized in that at least one sugar alcohol, the iron content of which is less than $6.5 \times 10^{-4}$ mmol/mol of sugar alcohol, is used for the formulation.

15. A process for preparing an aqueous pharmaceutical formulation of moxifloxacin or a salt thereof, characterized in that monosaccharide(s), the iron contents of which are less than $6.5 \times 10^{-4}$ mmol/mol of monosaccharide(s), are used for the formulation.

16. A process for preparing an aqueous pharmaceutical formulation of moxifloxacin or a salt thereof, characterized in that disaccharide(s), the iron contents of which are less than $6.5 \times 10^{-4}$ mmol/mol of disaccharide(s), are used for the formulation.

17. A process for preparing an aqueous formulation of moxifloxacin or a salt thereof, wherein a solution of moxifloxacin or a salt thereof having a moxifloxacin concentration or moxifloxacin salt concentration of from more than 0.2% (w/v) to the saturation concentration at room temperature of moxifloxacin or the salt thereof is, using a sugar- or sugar-alcohol-containing infusion carrier solution, adjusted to a use concentration suitable for parenteral administration.

18. A process as claimed in claim 17, wherein a solution of moxifloxacin hydrochloride having a concentration of from more than 0.2% (w/v) to 2.4% (w/v) (based on the amount of moxifloxacin) is used.

19. A pharmaceutical composition for parenteral administration comprising an aqueous solution of moxifloxacin hydrochloride in water having a moxifloxacin hydrochloride concentration (based on the amount of moxifloxacin) of from more than 0.2% (w/v) to 2.4% (w/v).

20. A combination preparation comprising an aqueous solution of moxifloxacin hydrochloride in water having a moxifloxacin hydrochloride concentration (based on the amount of moxifloxacin) of from more than 0.2% (w/v) to 2.4% (w/v) and an aqueous solution comprising sugar or sugar alcohols, wherein said solutions are separated from one another.

21. The aqueous pharmaceutical formulation as claimed in claim 4, characterized in that it comprises glucose as isotonizing agent.

22. The aqueous pharmaceutical formulation as claimed in claim 4, characterized in that it is prepared using at least one monosaccharide or oligosaccharide, the iron contents of which are less than $6.5 \times 10^{-4}$ mmol/mol of monosaccharide or oligosaccharide.

23. The aqueous pharmaceutical formulation as claimed in claim 5, characterized in that it is prepared using sugar alcohol, the iron content of which is less than less than $6.5 \times 10^{-4}$ mmol/mol of sugar alcohol.

24. An aqueous pharmaceutical formulation as claimed in claim 4, characterized in that it comprises moxifloxacin hydrochloride.

25. An aqueous pharmaceutical formulation as claimed in claim 5, characterized in that it comprises moxifloxacin hydrochloride.

26. An aqueous pharmaceutical formulation as claimed in claim 6, characterized in that it comprises moxifloxacin hydrochloride.

27. An aqueous pharmaceutical formulation as claimed in claim 7, characterized in that it comprises moxifloxacin hydrochloride.

28. An aqueous pharmaceutical formulation as claimed in claim 8, characterized in that it comprises moxifloxacin hydrochloride.

29. An aqueous pharmaceutical formulation as claimed in claim 9, characterized in that it comprises moxifloxacin hydrochloride.

30. An aqueous pharmaceutical formulation as claimed in claim 4 for parenteral administration to humans and animals.

31. An aqueous pharmaceutical formulation as claimed in claim 5 for parenteral administration to humans and animals.

32. An aqueous pharmaceutical composition as claimed in claim 6 for parenteral administration to humans and animals.

33. An aqueous pharmaceutical composition as claimed in claim 7 for parenteral administration to humans and animals.

34. An aqueous pharmaceutical composition as claimed in claim 8 for parenteral administration to humans and animals.

35. An aqueous pharmaceutical composition as claimed in claim 9 for parenteral administration to humans and animals.

* * * * *